United States Patent
Renda

(10) Patent No.: US 12,390,357 B2
(45) Date of Patent: Aug. 19, 2025

(54) INCONTINENCE AND STOMA SCENT PATCH

(71) Applicant: Nicola Renda, Horgen (CH)

(72) Inventor: Nicola Renda, Horgen (CH)

(*) Notice: Subject to any disclaimer, the term of this patent is extended or adjusted under 35 U.S.C. 154(b) by 481 days.

(21) Appl. No.: 17/778,912

(22) PCT Filed: Nov. 22, 2019

(86) PCT No.: PCT/EP2019/082321
§ 371 (c)(1),
(2) Date: May 23, 2022

(87) PCT Pub. No.: WO2021/098976
PCT Pub. Date: May 27, 2021

(65) Prior Publication Data
US 2023/0117300 A1    Apr. 20, 2023

(51) Int. Cl.
*A61F 13/84* (2006.01)
*A61F 5/441* (2006.01)
(Continued)

(52) U.S. Cl.
CPC .......... *A61F 5/441* (2013.01); *A61F 13/8405* (2013.01); *A61L 9/014* (2013.01); *A61L 9/042* (2013.01); *A61L 9/12* (2013.01); *B32B 5/022* (2013.01); *B32B 5/028* (2013.01); *B32B 5/265* (2021.05); *B32B 27/12* (2013.01); *B32B 27/16* (2013.01); *B32B 27/32* (2013.01); *A61F 2013/15121* (2013.01); *A61F 2013/8408* (2013.01); *B32B 2255/10* (2013.01); *B32B 2255/26* (2013.01); *B32B 2262/0253* (2013.01); *B32B 2262/0261* (2013.01); *B32B 2262/0276* (2013.01); *B32B 2262/062* (2013.01); *B32B 2262/14* (2013.01); *B32B 2307/54* (2013.01); *B32B 2307/726* (2013.01); *B32B 2307/732* (2013.01); *B32B 2307/748* (2013.01); *B32B 2307/758* (2013.01); *B32B 2556/00* (2013.01)

(58) Field of Classification Search
CPC .............. A61F 13/0253; A61F 13/0259; A61F 13/0226; A61F 13/0256
See application file for complete search history.

(56) References Cited

U.S. PATENT DOCUMENTS 4,880,690 A * 11/1989 Szycher ................. B32B 27/18
427/520
6,162,457 A * 12/2000 Martz ..................... A61L 15/46
428/905

(Continued)

FOREIGN PATENT DOCUMENTS

CH         713626 A2    9/2018
EP         0670685 B1   1/1997

OTHER PUBLICATIONS

International Search Report mailed on Aug. 6, 2020, in connection with corresponding International Application No. PCT/EP2019/082321; 3 pages.

*Primary Examiner* — Susan S Su
*Assistant Examiner* — Erin A Kim
(74) *Attorney, Agent, or Firm* — McCormick, Paulding & Huber PLLC

(57) ABSTRACT

An adhesive device is capable of releasing fragrances, specifically scent patches. The adhesive device is used in the treatment of side effects associated with incontinence or an ileostomy.

20 Claims, 1 Drawing Sheet

(51) Int. Cl.
*A61L 9/014* (2006.01)
*A61L 9/04* (2006.01)
*A61L 9/12* (2006.01)
*B32B 5/02* (2006.01)
*B32B 5/26* (2006.01)
*B32B 27/12* (2006.01)
*B32B 27/16* (2006.01)
*B32B 27/32* (2006.01)
*A61F 13/15* (2006.01)

(56) References Cited

U.S. PATENT DOCUMENTS

| | | | | |
|---|---|---|---|---|
| 8,058,500 | B2 | 11/2011 | Sojka et al. | |
| 2005/0261655 | A1* | 11/2005 | Nijs | A61F 13/5519 604/385.06 |
| 2006/0251609 | A1* | 11/2006 | Sojka | B32B 27/36 424/76.1 |
| 2007/0282238 | A1* | 12/2007 | Madsen | A61F 13/023 602/57 |
| 2018/0064588 | A1* | 3/2018 | Sturgis | A61F 13/8405 |
| 2019/0099300 | A1* | 4/2019 | Ogawa | A61L 15/22 |

* cited by examiner

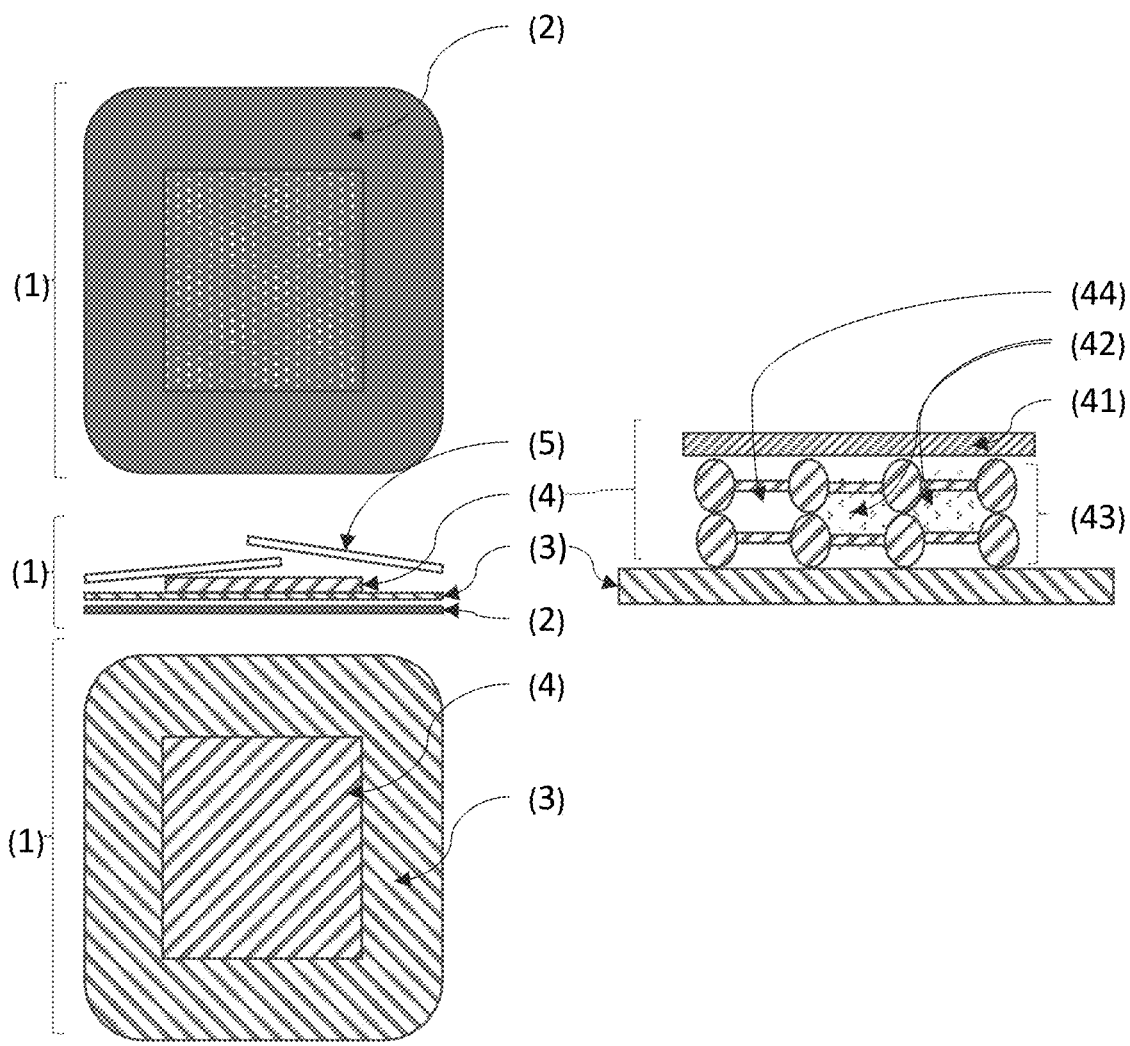

INCONTINENCE AND STOMA SCENT PATCH

CROSS-REFERENCE TO RELATED APPLICATION

This application is a National Stage application of International Patent Application No. PCT/EP2019/082321, filed on Nov. 22, 2019, which is hereby incorporated by reference in its entirety.

TECHNICAL FIELD

The present invention relates to adhesive devices capable of releasing fragrances. Such devices are also known as scent patch, fragrance strip and flavour stickers. The invention relates further to the manufacturing thereof and the use thereof.

BACKGROUND

The above adhesive devices are known per se and described e.g. in CH713626. Although suitable, the known scent patches show insufficient release profiles and shelf life. Further, acceptance by persons in need thereof is sometimes limited.

Accordingly, there is a need for providing improved patches allowing improved treatments to persons in need thereof. Thus, it is an object of the present invention to mitigate at least some of these drawbacks of the state of the art. In particular, it is an aim of the present invention to provide improved scent patches.

SUMMARY

These objectives are achieved by a scent patch according to claim 1. Further aspects of the invention are disclosed in the specification and independent claims, preferred embodiments are disclosed in the specification and the dependent claims.

The present invention will be described in more detail below. It is understood that the various embodiments, preferences and ranges as provided/disclosed in this specification may be combined at will. Further, depending of the specific embodiment, selected definitions, embodiments or ranges may not apply.

As used herein, the term "a", "an", "the" and similar terms used in the context of the present invention (especially in the context of the claims) are to be construed to cover both the singular and plural unless otherwise indicated herein or clearly contradicted by the context. As used herein, the terms "including", "containing" and "comprising" are used herein in their open, non-limiting sense.

BRIEF DESCRIPTION OF THE DRAWINGS

The present invention will be better understood by reference to the FIGURES.

FIG. 1 (left) schematically shows a top view, side view and bottom view of an inventive scent patch and (right) schematically shows an enlarged section of the adsorbing pad. List of References:
(1) scent patch
(2) backing layer
(3) adhesive layer
(4) adsorbing pad with pad supporting material (43), reservoir volume (44) containing fragrance composition (42, not shown) and anti-adhering layer (41)
(5) protective liner

DETAILED DESCRIPTION

In more general terms, in a first aspect, the invention relates to an improved scent patch, particularly an incontinence & stoma scent patch. This aspect of the invention shall be explained in further detail below, also referring to the figures and the example below.

Compared to the patches known, the inventive patches show an improved distribution profile of fragrances. Particularly, long a lasting continuous release is ensured. Further, an improved shelf life of the patches could be achieved. Finally, overall acceptance by persons in need thereof could be improved. Without being bound to theory, it is believed these beneficial effects are achieved by the combination of features according to claim 1.

Broadly speaking, the invention provides for a scent patch (1) comprising a backing layer (2), an adhesive layer (3), an adsorbing pad (4) and optionally one or more protective liners (5), wherein the adsorbing pad (4) comprises a support material (43) which comprises fragrance composition (42) and the support material (43) is complemented with an anti-adhering layer (41) opposite to the adhesive layer (3).

Advantageous embodiment of this patch and the elements constituting the same are discussed below.

Backing Layer (2): Backing layers are known in the field; suitable are fabric layers with a tensile strength >25 N/cm.

In embodiments of the invention, the backing layer (2) is a cotton-polyamide blended fabric, such as a 65% cotton-35% polyamide blended fabric.

In embodiments of the invention, the backing layer (2) is of white colour. Although it may, at a first glance, seem to be a simple matter of design choice, acceptance of scent patches is substantially increased when compared to conventional brownish patches.

Adhesive Layer (3): Adhesive layers are known in the field, suitable adhesive layers are resistant towards alcoholic compositions, particularly compositions containing (i.e. comprising or consisting of) ethanol ("ethanolic compositions").

The material of the adhesive layer may be selected from a broad range of known materials, preferably polymers. As the inventive scent patches are not applied to the skin, a broad range of adhesives may be used. Limitations of traditional patches therefore do not apply.

In embodiments of the invention the adhesive layer (3) is an acrylic polymer layer.

Adsorbing pad (4): The adsorbing pat is a key element of the inventive scent patch. It comprises a supporting material (43), a fragrance composition (42) and optionally an anti-adhering layer (41). The support material comprises a plurality of small fluid reservoir volumes (44) formed by supporting material (43).

Support material (43): Supporting materials are known in the field, suitable are non-woven pads; these pads comprise a fragrance composition (42). Typically, the non-woven pad has an absorbance capacity for said fragrance composition (42) of more than 20 g/100 cm2. Such adsorbance capacity allows for a long-lasting effect of the scent patch, once applied. According to the invention, the supporting material is a structured elastic material that is adaptively formed. Upon physical movements, eg. when walking, sitting down or turning in bed, tensions are created in the patch between support material (43) and adhesive layer (3), resulting in small short-term openings between protrusions of the reservoir volume (44).

In embodiments of the invention, the supporting material contains elastic longitudinal fibres arranged between the support material (43) and the reservoir volume (44). In this embodiment, the length shear of the volume can be kept small and the opening times between the protrusions are short. This allows for a long-term continuous release of fragrance molecules.

In embodiments of the invention, the support material (43) contains, particularly consists of, a non-woven viscose-polyester pad.

Anti-Adhering layer (41): The support material (43) may or may not be complemented with an anti-adhering layer on one side. Advantageously, the adsorbing pad (4) comprises a support material (43) and an anti-adhering layer (41). Within the inventive scent patch, the anti-adhering layer (41) is arranged opposite to the adhesive layer (3).

In embodiments of the invention, the anti-adhering layer (41) is a polyolefine net, such as a PE net.

Fragrance composition (42): Fragrance compositions are known in the field. The aroma thereof may be selected on the specific needs and preferences is the intended market. Fragrance molecules are commercial items, either as individual compounds, as a fragrance composition ("oil") or in dissolved form. Suitably, the fragrance composition (42) is a solution of fragrance molecules in alcohol or alcohol 1 water, such as ethanol or ethanol/water.

In embodiments of the invention the fragrance composition (42) comprises fragrance molecules selected from the consisting of group esters, alcohols, cycloalkenes, benzopyrones, and terpenes. Esters include, among others, benzylbenzoate and benzyl salicylate. Alcohols include, among others, benzyl alcohol. Benzopyrones include, amont others, cumarine. Terpenes include, among others, citral, citronellol, geraniol, limonene. The fragrance composition may comprise one or more different fragrance molecules, preferably a combination of 5-20 different fragrance moleducles. As the inventive scent patch is not in direct contact with the human skin, skin irritation or allergic reactions are of minor concern. This allows selection of a broad range of fragrance molecules and of comparatively high dosage of fragrance molecules. Suitable dosages are those commonly known for eau de cologne (4-8 wt % of fragrance oil), eau de toilette (8-12 wt % of fragrance oil), eau de parfume (8-15 wt % of fragrance oil), parfumes (15-30 wt % of fragrance oil) and even higher.

Protective Liners (5): Protective liners are known in the field, suitable are films with a thickness below 100 micron. Protective liners may be arranged as partially overlapping liners or with matching geometry.

In embodiments of the invention, the protective liner (5) is a siliconized polyolefine film, such as a siliconized PE film.

Scent patch (1): The dimensions of and shape of inventive scent patch may vary over a broad range.

In embodiments of the invention, the scent patch has a total surface area between 2-60 cm2, preferably 16-36 cm2. Suitable are, for example the following dimensions: 10*6 cm, 10*4 cm, 6*6 cm, 6*5 cm, 6*4 cm, 5*5 cm, 5*4 cm, 4*4 cm.

In embodiments of the invention, the adsorbing pad (4) has a total surface area between 1-45 cm2, preferably 9-25 cm2. Suitable are, for example the following approximate dimensions: 9*5 cm, 9*3 cm, 5*5 cm, 5*4 cm, 5*3 cm, 4*4 cm, 4*3 cm, 3*3 cm and 3.6*2 cm.

In embodiments of the invention, the scent patch has a maximum thickness between 0.5-5 mm, such as 1-2 mm. It is considered advantageous to provide such a thin and nevertheless long-lasting scent patch.

In embodiments of the inventions, the scent patch is rectangular or round, preferably rectangular with rounded edges.

In embodiments of the invention, the adsorbing pad (4) is fully surrounded by adhesive layer (3), as shown in FIG. 1. This arrangement allows for reliable adhesion, e.g. to the diaper/nappy inlay.

Sachet (6): The inventive scent patch may be packed in a sachet (6) as known in the field. Such sachet being a primary package for the inventive scent patch. Suitable sachets preferably containing two sealable composite films (61). Again such films being known, typically comprising the following layers: PET-adhesive-Aluminium-adhesive-PE.

The sachet described herein is a suitable Primary Package for the inventive scent patches. The specific combination of sachet and scent patch allows for both, simple use and prolonged shelf life. In embodiments of the invention, a shelf life of 5 years is observed.

Suitable sachets contain two sealable composite laminates (61), particularly sealable aluminium laminates. Such laminates may comprise a PET coating on one side and a PE coating on the opposite site of the aluminium laminate. Such composite laminates are known per se. Typically, adhesive layers allow for reliable bonding of PE an PET coating to the aluminium layer in the composite laminate (61). It is preferred to include one scent patch (1) within one sachet (6).

Kit (7): The inventive scent patch may be delivered to the user in the form of a kit. Such kit (7) comprising a multitude of scent patches, preferably scent patches packed in a primary package such as described above, and instructions for use the patch. Accordingly, such kit may be considered a secondary package.

In a second aspect, the invention relates to the use of scent patches as described herein. This aspect of the invention shall be explained in further detail below:

As outlined above, the inventive scent patches enable a prolonged and nearly continuous release of fragrance molecules to the environment. The inventive scent patches fundamentally differ from pharmaceutical patches (which are also called transdermal devices).

Pharmaceutical patches are applied to the patient's skin. They are adapted to release pharmaceutically active ingredients from the patch through the skin into the human circulatory system. To the contrary, the inventive scent patches are not applied to the patient's skin. Rather, they are placed on the persons' clothing or a device the person/patient is wearing close to his body. Such devices include diapers, nappy inlays and the like. Further, the inventive scent patches are adapted to release fragrances from the patch away from the person into the environment.

The inventive scent patches are easy to use, thereby increasing acceptance by affected persons and nursing staff. Inventive patches may be applied/used by removing the protective liner (5) from the patch, adhering the thus obtained patch on the clothing of a human being or an item close to the human being (particularly a diaper or a nappy inlay) and retaining the patch in its position for at least 2-4 hours. By applying the patch in this way, minimum effort is required by the nursing staff and the person receiving such patch is not affected at all. This is considered a significant advantage and clearly increases acceptance.

Due to its beneficial effects, the invention also provides for the use of a scent patch as described herein to treat/ alleviate side effects of an ileostomy. An Ileostomy is a surgical opening constructed by bringing the end or loop of small intestine out onto the surface of the skin. This is only done in case of severe diseases. It is apparent that the inventive scent patch does not address such underlying severe disease. Rather, it helps people suffering from such severe disease to participate in normal social life or at least to welcome relatives and nursing staff. The scent patch may thus also be termed stoma scent patch.

Due to its beneficial effects, the invention also provides for the use of a scent patch as described herein to treat/alleviate side effects of incontinence. It is clear that the scent patch does not treat incontinence itself. However, it helps persons affected with this disorder to participate in normal social life. The scent patch may thus also be termed Incontinence scent patch.

In a third aspect, the invention relates to the manufacturing of scent patches as described herein. This aspect of the invention shall be explained in further detail below:

For manufacturing, known technologies may be applied to the inventive scent patch. The individual components of such scent patch (fragrance composition, protective liner, backing layer, adhesive layer . . . ) are commercial items or are at least obtainable according to known procedures.

To further illustrate the invention, the following example are provided. This examples is provided with no intend to limit the scope of the invention.

A test series of scent patches as described herein, FIG. 1, is prepared and tested as follows.

1. The patches are each 6×4 cm and comprise a white CD elastic fabric, acrylic adhesive and white absorbing pad. The backing layer consists of elastic fibre 65% cotton, 35% Polyamnide with MD tensile strength >30 N/cm and weight 80-100 g/m2. The Adhesive is an acrylic polymer of 55-65 g/cm2 and resistant to ethanol. The adsorbing pad is a white viscose and polyester nonwoven material comprising the fragrance composition and a polyethylene net as anti-adhering layer, 2×3.6 cm. The fragrance composition is an ethanolic solution comprising terpenes, esters, alcohols, benzopyrones and cycloalkanes. The Patch is complemented with two siliconized LDPE films of 72-88 micron as a protective liner and packed in a sealed sachet of composite material (PET-Adhesive-Aluminium-Adhesive-PE).
2. The patch described above has a shelf life of 5 years, if stored in cool and dry conditions, far from light.
3. The patch described above was used in a care centre for elderly people during daily routine. Depending on the specific situation, the patch was applied once, twice or three times a day on the person's diaper/nappy inlay.
4. The following was observed by the nursing staff:
    The inventive scent patch successfully neutralized unpleasant odours, such unpleasant odours being inevitable until now when wearing diapers or inlays.
    The inventive scent patch was found simple and reliable in use, thereby increasing acceptances for both nursing staff, relatives and affected persons.
    Surprisingly, this simple measure significantly increased lust for life and well-being of affected persons.

While the present disclosure has been illustrated and described with respect to a particular embodiment thereof, it should be appreciated by those of ordinary skill in the art that various modifications to this disclosure may be made without departing from the spirit and scope of the present disclosure.

The invention claimed is:

1. A scent patch comprising, in the following sequence, a backing layer, an adhesive layer, an adsorbing pad and optionally one or more protective liners, wherein:
    the backing layer is a fabric layer with a tensile strength >25 N/cm;
    the adhesive layer is a polymer layer resistant to ethanol/ethanolic compositions;
    the adsorbing pad comprises a non-woven pad which comprises a fragrance composition and which has an absorbance capacity for said fragrance composition of more than 20 g/100 cm2; the absorbing pad further comprises an anti-adhering layer opposite to the adhesive layer;
    the protective liner is a film with a thickness below 100 microns; and
    the non-woven pad and the adjacent adhesive layer are configured to interact during use of the scent patch, thereby creating tensions therebetween which result in short-term openings for gradually releasing the fragrance composition.

2. The scent patch according to claim 1, wherein the backing layer is a cotton-polyamide blended fabric.

3. The scent patch according to claim 1, wherein the adhesive layer is an acrylic polymer layer.

4. The scent patch according to claim 1, wherein the adsorbing pad comprises a non-woven viscose-polyester pad comprising the fragrance composition.

5. The scent patch according to claim 1, wherein the fragrance composition is a solution of fragrance molecules in ethanol or ethanol/water.

6. The scent patch according to claim 1, wherein the fragrance composition comprises one or more fragrances selected from the group consisting of esters, alcohols, cycloalkenes, benzopyrones, and terpenes.

7. The scent patch according to claim 1, wherein the anti-adhering layer is a polyolefin net.

8. The scent patch according to claim 1, wherein the protective liner is a siliconized polyolefin film.

9. The scent patch according to claim 1, having
    a total surface area between 1-60 cm2;
    the adsorbing pad is fully surrounded by adhesive layers; and/or
    the maximum thickness of the scent patch is between 0.5-5 mm.

10. Use of a scent patch according to claim 1 comprising the steps of:
    removing the protective liner,
    adhering the patch on the clothing of a human being; or an item close to the human being; and
    retaining the patch in its position for at least 2-4 hours.

11. A scent patch according to claim 1, packed in a sachet, the sachet containing two sealable composite films, said films comprising the following layers: PET-adhesive aluminum-adhesive-PE.

12. A kit (7) comprising a multitude of patches according to claim 11 and instructions for use comprising the steps of removing the protective liner; adhering the patch on the clothing of a human being, or an item close to the human being; and retaining the patch in its position for at least 2-4 hours.

13. Use of a scent patch according to claim 1 to treat/alleviate side effects of an ileostomy.

14. Use of a scent patch according to claim 1 to treat/alleviate side effects of incontinence.

15. A method for manufacturing a scent patch according to claim 1 comprising the steps of:

providing a backing layer; followed by coating said backing layer with an adhesive layer; followed by fixing adsorbing pads in predetermined positions on said adhesive layer; followed by covering the thus obtained intermediate product with protective liners; and cutting the thus obtained product into desired size and shape to thereby obtain the inventive scent patch.

16. The method according to claim 15, further comprising:

packing the thus obtained scent patch into sachets by sealing the scent patch between two composite films; and assembling a multitude of these packed scent patches and instructions for use to a kit.

17. The scent patch according to claim 9, having a total surface area between 16-32 cm2.

18. A scent patch comprising, in the following sequence, a backing layer, an adhesive layer and an adsorbing pad, wherein:

the backing layer is a fabric layer with a tensile strength >25 N/cm;

the adhesive layer is a polymer layer resistant to ethanol/ethanolic compositions;

the adsorbing pad comprises a non-woven pad which includes a fragrance composition and which has an absorbance capacity for said fragrance composition of more than 20 g/100 cm2; and wherein the non-woven pad contains elastic longitudinal fibers and wherein the adsorbing pad includes a plurality of small fluid reservoir volumes formed by the non-woven pad.

19. The scent patch according to claim 18, further comprising one or more protective liners, wherein the protective liner is a film with a thickness below 100 microns, and wherein the adsorbing pad further comprises an anti-adhering layer opposite to the adhesive layer.

20. The scent patch according to claim 18, wherein the non-woven pad and the adjacent adhesive layer are configured to interact during use of the scent patch, thereby creating tensions therebetween.

* * * * *